United States Patent [19]

Matsushima et al.

[11] 4,296,094

[45] Oct. 20, 1981

[54] DENTAL CLEANING COMPOSITION AND METHOD

[75] Inventors: Yoshio Matsushima; Teruhiko Kumura; Isamu Kawamura, all of Takamatsu; Terushige Kawata, Tokushima, all of Japan

[73] Assignee: Kyowa Chemical Industry Co., Ltd., Tokyo, Japan

[21] Appl. No.: 155,165

[22] Filed: Jun. 2, 1980

[51] Int. Cl.³ .......................... A61K 7/16; A61K 7/18
[52] U.S. Cl. .......................................... 424/49; 424/52
[58] Field of Search ................................... 424/49–58, 424/154; 51/307–309

[56] References Cited

U.S. PATENT DOCUMENTS 3,539,306 11/1970 Kumura et al. ...................... 424/154
3,650,704 3/1972 Kumura et al. ...................... 424/154

FOREIGN PATENT DOCUMENTS 46-2280 1/1971 Japan.
47-32198 8/1972 Japan.
48-82021 11/1973 Japan.
50-830226 9/1975 Japan.
51-856384 8/1976 Japan.
52-3353 1/1977 Japan.
53-5633 3/1978 Japan.
55-45619 3/1980 Japan.

*Primary Examiner*—Shep K. Rose
*Attorney, Agent, or Firm*—Sherman & Shalloway

[57] ABSTRACT

A dental cleaning composition comprising about 0.01 to about 30% by weight, based on the composition, of a hydrotalcite compound of the following formula $$Mg_{1-x}Al_x(OH)_{2+x-ny}A_y^{n-} \cdot mH_2O$$

wherein
$A^{n-}$ represents an anion having a valence of n, x is a positive number represented by $0 < x < 0.5$,
y is a positive number represented by $0 < y \leq 0.5$, and
m is a positive number represented by $0 < m < 2$, and a dentally acceptable carrier or diluent; and a method for dental cleaning with the use of the above composition.

12 Claims, No Drawings

DENTAL CLEANING COMPOSITION AND METHOD

This invention relates to a dental cleaning composition which is expected to have an effect of preventing dental caries by its ability to adsorb and remove bacteria in the oral cavity and to neutralize acids produced by these acids, and to a method for dental cleaning with the use of this composition.

More specifically, this invention pertains to a dental cleaning composition comprising about 0.01 to about 30% by weight, based on the composition, of a hydrotalcite compound of the following formula $$Mg_{1-x}Al_x(OH)_{2+x-ny}A_y^{n-} \cdot mH_2O \qquad (1)$$

wherein $A^{n-}$ represents an anion having a valence of n, x is a positive number represented by $0 < x < 0.5$, y is a positive number represented by $0 < y \leq 0.5$, and m is a positive number represented by $0 < m < 2$, and a dentally acceptable carrier or diluent. It also pertains to a method for cleaning teeth with the compound of formula (1).

Various causes have previously been assigned to the mechanism of dental caries, but no definite theory has yet been established. It is at least known however that bacteria living in the oral cavity and foods which form a substrate for growth and proliferation of these bacteria and lead to formation of materia alba are indirect factors.

It is well known that to cope with the latter factor, it is desirable to remove fully food residues that may remain in the oral cavity, especially in the depressed parts of the teeth and the spaces between the teeth. However, no effective and safe measure against the bacteria in the oral cavity has yet been realized to date. For example, it may be possible to control these bacteria by using suitable antibiotics or bactericides. But in view of the environment of the oral cavity, this controlling measure cannot be achieved by a single dose of such a drug, and it must be administered continuously or repeatedly. Moreover, the side-effects and stimulation of these drugs on the entire body or local mucous membranes are by no means negligible, and continued administration may lead to development of drug-resistant bacteria.

It has now been found in accordance with this invention that the hydrotalcite compounds of formula (1) given hereinabove which have not been suggested at all for use as an ingredient of a dentifrice in the past act very effectively in removing bacteria in the oral cavity which may cause dental caries, and that these hydrotalcite compounds produce unexpected excellent effects over conventional dentifrices when used as an active ingredient of a dental cleaning composition.

It has also been found that the hydrotalcite compounds rapidly react with acids such as lactic acid which may be produced by these bacteria in the oral cavity to neutralize them; that as demonstrated by their use as antacids, these hydrotalcite compounds are non-toxic compounds and cause no trouble even when swallowed down by accident and are unlikely to cause any side-effect in repeated use; that these hydrotalcite compounds are tasteless and odorless, give no stimulation to the mucous membrane of the oral cavity, and are pleasing to the palate in persons of all ages; and that these hydrotalcite compounds are inexpensive and can also be used in combination with conventional dentifrice ingredients. In view of their outstanding effect of removing bacteria in the oral cavity and additional advantages mentioned above, the hydrotalcite compounds of formula (1) have been found to be a unique and noteworthy ingredient of a dental cleaning composition which can be applied by the usual practice of brushing, washing, etc.

Investigations of the present inventors have shown that the hydrotalcite compounds of formula (1) have a strong positive charge on the surfaces of their crystal grains. They presume that this is an important factor which is conducive to adsorption and removal of bacteria having a negative charge.

It is an object of this invention to provide a dental cleaning composition having an effect of removing bacteria in the oral cavity.

The above and other objects of this invention along with its advantages will become more apparent from the following description.

The dental cleaning composition of this invention comprises about 0.01 to about 30% by weight, based on the entire composition, of the hydrotalcite compound of formula (1) and a carrier or diluent.

The hydrotalcite compounds of formula (1) used in this invention are known, and methods for their preparation are disclosed, for example, in Japanese Pat. Nos. 649629, 830226, 678273 and 856384, and Japanese Laid-Open Patent Publications Nos. 69780/73, 82021/73 and 18789/74.

Preferably, the hydrotalcite of formula (1) used in this invention is in the form of a powder in which the secondary particles have an average particle size of up to about 100 microns, preferably up to about 50 microns, more preferably up to about 10 microns, for example about 0.01 to about 50 microns, especially about 0.01 to about 10 microns, in order to secure good dispersibility and good action of removing bacteria in the oral cavity.

The anion $A^{n-}$ in formula (1) may, for example, be $CO_3^{2-}$, $F^-$, $SO_4^{2-}$, $CH_3COO^-$, a tartaric acid anion, a citric acid anion, etc. Of these, $CO_3^{2-}$ and $F^-$ are preferred. The anion $A^{n-}$ may be a single anion or may consist of a plurality of anions. When two or more anions are included, y in $A_y^{n-}$ is the sum of y values in these anions.

The dental cleaning composition of this invention may be in various forms, for example in the form of conventional dentifrices such as a powder dentifrice, a paste dentifrice, a cream dentifrice or a liquid dentifrice, or in the form of a suspension for gargling or washing under fluid pressure.

The dental cleaning composition of this invention may contain a liquid or solid carrier or diluent for dentifrices as the dentally acceptable carrier or diluent. Examples of such carriers or diluents are polishing agents, moisture-retaining agents, binders, foaming agents, water which are normally used in dentifrices. The dental cleaning composition of this invention may also contain additives such as perfumes, sweetenings, germicides, etc. which are normally used in dentifrices. These carriers or diluents or additives may be used singly or as a mixture.

Examples of the polishing agents are calcium phosphate, calcium carbonate, calcium sulfate, aluminum hydroxide, magnesium carbonate and inert sodium meta-phosphate. Examples of the moisture-retaining agents are glycerol, sorbitol, propylene glycol and polyethylene glycol. Useful binders include gum arabic, sodium alginate, carboxymethyl cellulose, poly(sodium acrylate). Useful foaming agents are, for example, sodium laurylsulfate, sodium laurylsulfonate, and alkylarylsulfonic acids. The perfumes include methanol, spearmint, cinnamon, wintergreen and other various perfumes of floral, fruit and woody notes. The sweetenings include saccharin and sorbitol. Examples of the germicides are sodium benzoate, methyl p-hydroxybenzoate, ethyl p-hydroxybenzoate, butyl p-hydroxybenzoate, i-butyl p-hydroxybenzoate, and i-propyl p-hydroxybenzoate. Many additives for dentifrices are known, and can be properly chosen even if they are not included in the above exemplification.

The amount of the carrier or diluent can be properly selected, and is, for example, about 35 to about 97% by weight for the polishing agents, about 25 to about 40% by weight for the moisture-retaining agents, about 1 to about 5% by weight for the binders, and about 1 to about 2% by weight for the foaming agents, about 0.1 to about 3% by weight for the perfumes, and about 0.01 to about 3% by weight for the sweetenings, all based on the weight of the composition. These amounts are only illustrative, and suitable amounts may be chosen depending upon the types and combinations of these additives, the form of the dental cleaning composition, etc.

The hydrotalcite compound of formula (1) in the dental cleaning composition of this invention may be used in an amount of about 0.01 to about 30% by weight based on the weight of the composition. If desired, its amount may exceed 30% by weight. When the dental cleaning composition is in the form of a conventional dentifrice, its amount is preferably about 1 to about 30% by weight. When the composition is in the form of a suspension for gargling or fluid-pressure washing, the amount of the hydrotalcite compound may be about 0.01 to about 10% by weight, preferably about 0.01 to about 6% by weight, based on the weight of the composition. Such a suspension is preferably an aqueous suspension.

When the dental cleaning composition is to be used by means of a tooth brush for preventive purposes, it is suitably in the form of a powder or a paste containing a small amount of water.

For the best result in preventing dental caries, the hydrotalcite compound of formula (1) is used singly without incorporating any additives. Several brushings or garglings after meals, preferably 3 to 6 times a day, are recommended.

Accordingly, the present invention also provides a method for cleaning teeth which comprises washing the teeth with an effective amount for cleaning of the hydrotalcite compound of formula (1).

The following Examples and Comparative Examples illustrate the present invention more specifically.

EXAMPLES 1 to 5

Five subjects were caused to brush their teeth after lunch using about 1 g of each of the hydrotalcite compounds shown in Table 1 (the secondary particles having an average particle size of about 0.5 to about 5 microns). About one hour later, a cariostat test was conducted by the following procedure.

A cariostat test method [see T. Simono, Shika Tenbo, 46, 941 (1975)] was used. A cariostat applicator was rubbed against the teeth and pulp of each of the subjects, and then dipped in a cariostat ampoule solution. A change in the color of the ampoule solution was examined 24 hours later. If no bacterium in the oral cavity existed in the ampoule solution, it showed a blue color. According to the amount of remaining bacteria, the color of the ampoule solution changed to green, yellowish green, and to yellow. When the color turned yellow, the bacteria in the oral cavity were very active and produced lactic acid, etc. which become a cause of dissolving of the dental enamel. By the above procedure, the same test was conducted for 3 days.

The results are shown in Table 1.

COMPARATIVE EXAMPLE

Three subjects were caused to brush their teeth after lunch by using a marketed dentifrice, and the results were evaluated by the same cariostat testing method as in Examples 1 to 5 one hour after brushing. The results are also shown in Table 1.

TABLE 1

| Example | Active ingredient | Results of the cariostat test (*) | | | |
|---|---|---|---|---|---|
| | | Blue | Green | Yellow-ish | Yellow |
| 1 | $Mg_{0.66}Al_{0.34}(OH)_2(CO_3)_{0.17} \cdot 0.48H_2O$ | 15 | | | |
| 2 | $Mg_{0.75}Al_{0.25}(OH)_2(CO_3)_{0.125} \cdot 0.50H_2O$ | 15 | | | |
| 3 | $Mg_{0.9}Al_{0.1}(OH)_2(CO_3{0.05} \cdot 0.38H_2O$ | 14 | 1 | | |
| 4 | $Mg_{0.7}Al_{0.3}(OH)_2F_{0.3} \cdot 0.24H_2O$ | 15 | | | |
| 5 | $Mg_{0.75}Al_{0.25}(OH)_{1.9}(SO_4)_{0.13} \cdot 0.41H_2O$ | 15 | | | |
| Comparative Example | Marketed dentifrice | | | | 9 |

(*) Total number of detreminations of color in the three days' test on five subjects.

FORMULATION EXAMPLE 1

| Ingredient | Parts by weight |
|---|---|
| $Mg_{0.7}Al_{0.3}(OH)_2(CO_3)_{0.15} \cdot 0.55H_2O$ | 30.5 |
| Sorbitol (70% aqueous solution) | 15.2 |
| Glycerol | 15.2 |
| Saccharin sodium | 0.1 |
| l-Menthol | 0.1 |
| Neomekkins (*) | 1.0 |
| Distilled water | 37.i |
| | 100.0 |

(*) Butyl p-hydroxybenzoate 15 parts by weight
i-Butyl p-hydroxybenzoate 15 parts by weight
i-Propyl p-hydroxybenzoate 20 parts by weight
Distilled water 50 parts by weight

FORMULATION EXAMPLE 2

| Ingredient | Parts by weight |
|---|---|
| $Mg_{0.65}Al_{0.35}(OH)_2(CO_3)_{0.175} \cdot 0.47_2O$ | 14.4 |

-continued

| Ingredient | Parts by weight |
|---|---|
| Calcium carbonate | 18.2 |
| Sorbitol (70% aqueous solution) | 14.7 |
| Methyl cellulose | 0.8 |
| Glycerol | 14.7 |
| Saccharin sodium | 0.1 |
| Spearmint oil | 1.0 |
| Neomekkins | 1.0 |
| Distilled water | 35.1 |
| | 100.0 |

FORMULATION EXAMPLE 3

| Ingredient | Parts by weight |
|---|---|
| $Mg_{0.8}Al_{0.2}(OH)_2(CO_3)_{0.1}(SO_4)_{0.1}\cdot 0.3H_2O$ | 10.0 |
| Calcium secondary phosphate dihydrate | 25.5 |
| Sorbitol (70% aqueous solution) | 18.8 |
| Glycerol | 12.5 |
| Methyl cellulose | 1.0 |
| Saccharin sodium | 0.1 |
| l-Menthol | 0.1 |
| Sucrose fatty acid ester | 1.5 |
| Neomekkins | 1.0 |
| Distilled water | 29.5 |
| | 100.0 |

What we claim is:

1. A dental cleaning composition comprising about 0.01 to about 30% by weight, based on the composition, of a hydrotalcite compound of the following formula $$Mg_{1-x}Al_x(OH)_{2+x-ny}A_y^{n-}\cdot mH_2O$$

wherein
$A^{n-}$ represents an anion having a valence of n,
x is a positive number represented by $0<x<0.5$,
y is a positive number represented by $0<y\leq 0.5$, and
m is a positive number represented by $0<m<2$, and
at least one dentally acceptable carrier or diluent selected from the group consisting of polishing agents, moisture-retaining agents, binders, and foaming agents.

2. The composition of claim 1 wherein $A^{n-}$ is an anion selected from $CO_3^{2-}$ and $F^-$.

3. The composition of claim 1 wherein the secondary particles of said hydrotalcite compound have an average particle size of up to about 100 microns.

4. The composition of claim 1 containing additionally water.

5. The composition of claim 1 which further comprises at least one member selected from the group consisting of dentifrice perfumes, dentifrice sweetenings and dentifrice germicides.

6. The composition of claim 1 which is in the form of a dentifrice selected from the group consisting of a powder dentifrice, a paste dentifrice and a cream dentifrice, and in which the amount of said hydrotalcite compound is about 1 to about 30% by weight of the composition.

7. The composition of claim 1 which is in the form of an aqueous suspension for gargling or fluid-pressure washing, and in which the amount of said hydrotalcite compound is about 0.01 to about 10% by weight based on the weight of the composition.

8. A method for cleaning teeth, which comprises brushing, gargling or fluid pressure washing the teeth with an effective amount for cleaning of a hydrotalcite compound of the formula $$Mg_{1-x}Al_x(OH)_{2+x-ny}A_y^{n-}\cdot mH_2O$$

wherein
$A^{n-}$ represents an anion having a valence of n,
x is a positive number represented by $0<x<0.5$,
y is a positive number represented by $0<y\leq 0.5$, and
m is a positive number represented by $0<m<2$,
and a dentally acceptable carrier or diluent.

9. The method of claim 8 wherein $A^{n-}$ in the formula is an anion selected from the group consisting of $CO_3^{2-}$ and $F^-$.

10. The method of claim 8 wherein the secondary particles of the hydrotalcite compound have an average particle size of up to about 100 microns.

11. The composition of claim 1 wherein the amounts of carrier or diluent used are from about 35 to 97% by weight for the polishing agents, from about 25 to 40% by weight for the moisture-retaining agents, from about 1 to about 5% by weight for the binders, and from about 1 to about 2% by weight for the foaming agents, all percentages being based on the weight of the composition.

12. The composition of claim 4 which is in the form of a suspension for gargling or washing under fluid pressure and in which the amount of the hydrotalcite compound is from about 0.1 to about 10% by weight, based on the weight of the composition.

* * * * *